United States Patent [19]

Maurice

[11] Patent Number: 5,334,831
[45] Date of Patent: Aug. 2, 1994

[54] PROXIMITY DETECTOR FOR DETECTING POSITION OF A TARGET

[75] Inventor: Lisa B. Maurice, Jericho, Vt.

[73] Assignee: Simmonds Precision Products, Inc., Akron, Ohio

[21] Appl. No.: 900,879

[22] Filed: Jun. 18, 1992

Related U.S. Application Data

[63] Continuation of Ser. No. 709,627, Jun. 3, 1991, Pat. No. 5,149,962.

[51] Int. Cl.$^5$ .............................................. H01J 5/16
[52] U.S. Cl. .................... 250/227.17; 250/227.21; 324/96
[58] Field of Search ............. 250/225, 227.17, 227.21, 250/231.10, 227.23; 324/96, 174, 175, 244.1, 260, 262

[56] References Cited

U.S. PATENT DOCUMENTS

| | | | |
|---|---|---|---|
| 4,554,449 | 11/1985 | Taniuchi et al. | 324/96 |
| 4,563,639 | 1/1986 | Langeac | 324/96 |
| 4,698,497 | 10/1987 | Miller et al. | 250/225 |
| 4,843,232 | 6/1989 | Emo et al. | 250/225 |
| 4,947,035 | 8/1990 | Zook et al. | 250/225 |
| 5,051,577 | 9/1991 | Lutz et al. | 250/227.17 |
| 5,059,783 | 10/1991 | Stranjord et al. | 250/227.21 |
| 5,061,847 | 10/1991 | Hazan et al. | 250/227.17 |
| 5,149,962 | 9/1992 | Maurice | 250/227.17 |

FOREIGN PATENT DOCUMENTS 0050912  2/1989  Japan ............... 250/227.21

OTHER PUBLICATIONS

Maurice et al. "Low Cost Binary Proximity Sensor for Automotive Applications"; SPIE vol. 1173 pp. 75–83 (1989).

Nagao, "Light Applied Measuring Apparatus"; Published Japanese Patent Application No. 62-90547(A) (Apr. 1987).

Tokumaru, "Light Application Measuring Instrument"; Published Japanese Patent Application No. 62-76474(A) (Apr. 1987).

*Primary Examiner*—David C. Nelms
*Assistant Examiner*—Stephone B. Allen
*Attorney, Agent, or Firm*—William E. Zitelli; Leonard L. Lewis

[57] ABSTRACT

A proximity detector apparatus that uses the Faraday Effect to detect position changes of a target. The proximity detector includes a permanent magnet having a magnetic field that changes as the target moves to or from a predetermined position. A self-referencing optical sensor is provided that detects the changed magnetic field. The optical sensor includes a magneto-optic material positioned near a node of the magnet. Means are provided to transmit polarized interrogation light along an optical path that includes the magneto-optic material. The optical path is bi-directionally addressed and is non-reciprocal. The optical sensor transduces the changed magnetic field into a modulation of the interrogation light's intensity. Means are provided to detect variations in the interrogation light intensity and to determine a ratio such as the difference over the sum ratio for two interrogation light samples that traveled the optic path in opposite directions.

7 Claims, 7 Drawing Sheets

PROXIMITY DETECTOR FOR DETECTING POSITION OF A TARGET

This is a continuation of pending application Ser. No. 07/709,627, filed Jun. 3, 1991, now U.S. Pat. No. 5,149,962.

BACKGROUND OF THE INVENTION

This application is related to my co-pending application Ser. No. 07/709,352 for Debris Monitoring System filed on even date herewith. The invention relates generally to proximity detectors used to determine position of a ferrous target with respect to a sensor. The invention also relates generally to apparatus and methods useful in detecting the presence of debris and contamination in fluids. More particularly, the invention relates to the detection and removal of magnetic debris from fluids, especially in applications where both the quantity and rate of debris accumulation in the fluid are important information. While the invention described herein is explained in connection with a lubricating oil type fluid, it will be appreciated that the invention is similarly useful in any liquid or gaseous fluid medium, or combination thereof.

The presence of contamination and debris in lubricating fluids such as machine and engine oils is clearly undesirable in most applications due to the attendant decrease in the fluid's capacity to protect moving parts from friction and wear. More significant, however, is that the presence of magnetic debris such as pieces of ferrous metal can be an indication of wear and damage in moving parts within the equipment. Early detection of such debris can be critical in applications such as gas turbine engines used in today's advanced aircraft. As the state of the art advances for such engines, failure rates tend to increase for the high performance engine parts. The ability to detect the onset of failure of moving engine components is imperative not only in military aircraft with high thrust to weight ratios, but also commercial aircraft with turbine engines that are operated for long periods of time. Early detection of critical part wear reduces repair costs, secondary engine damage, and unscheduled maintenance time. Of course, such early detection can be useful in many other applications besides aircraft engines where failure of moving lubricated parts results in significant repair costs and down time.

Prior attempts at detecting and capturing debris in fluids include electric chip detectors and magnetic chip detectors. Typically, such detectors are placed in the fluid returning from the engine in an oil scavenge line. Magnetic chip detectors are essentially just magnets that capture magnetic debris in the fluid. There is no real-time feedback available on the aircraft to indicate the status of the detector. Rather, during maintenance the magnetic chip detector must be removed for visual inspection.

Electric chip detectors function similarly to the magnetic chip detectors, except they further include an electrical continuity indication capability. Typically, two electrodes are positioned near a magnet such that captured particles eventually bridge a gap between the electrodes causing a change in continuity. While this approach can provide a rudimentary feedback signal to the cockpit, little or no quantitative or qualitative information can be discerned from such a signal. This approach also does not include any trending capability.

The data does not provide an indication of the quantity of material accumulated, nor the rate of accumulation. Knowing the rate of accumulation is a highly desirable feature because the rate of debris accumulation in the fluid is an excellent indication of the severity and rate of failure of the machine or engine parts. The electric chip detectors are also very susceptible to false indications due to spurious noise, background debris and electromagnetic interference.

The magnetic chip detectors, as well as the electric chip detectors, rely primarily on laboratory analysis of the collected debris to determine the condition of the equipment being monitored. That is, measurement of the debris particles and analysis of their total accumulation usually only occurs when maintenance personnel remove and visually inspect the sensors. The frequent inspection requirement, of course, is not only time consuming and costly, but also increases the likelihood of mistakes being made during teardown and reassembly. The lack of a real-time analysis is a significant drawback because substantial deterioration can occur between scheduled maintenance activities. Other types of oil debris monitoring systems are discussed in SAE publication AIR 1828 dated Mar. 1, 1984. Such systems include inductive debris monitors that produce electric pulses when debris contacts coils, and electro-optical monitors that use the scattering of light by debris in the fluid. These systems are still developmental and are subject to false indications and noise.

A known system that purports to provide both particle quantity and rate of occurrence on a real-time basis is described in U.S. Pat. No. 4,219,805 issued to Magee et al. This system detects large particles of two predetermined sizes (particles greater than 250 microns and particles greater than 1000 microns) by generating electric pulses upon impact of the particles with the magnetic sensor. These electric pulses are counted by an electronic analyzer to approximate both the quantity of accumulation and the rate of accumulation. The data can be recorded on a chart recorder for trend analysis during maintenance activity, and can also be viewed on a real-time basis to detect rapid catastrophic failures. The system, however, is still susceptible to spurious noise and electromagnetic interference near the sensor. Moreover, the need to constantly monitor electric pulses at the sensor output requires expensive and complicated electronic hardware. When multiple sensors are required, a situation that is quite common in aircraft applications, each sensor must be individually and continually monitored to avoid missing the effects of a particle impacting the sensor. This makes data multiplexing costly and difficult to implement. The system also ignores failure modes indicated by increased production of debris particles that are too small to trigger the sensor.

The use of optical transducers to detect variations in the intensity of a magnetic field modulated by a moving target is well known. One such application is detecting a rotating target to discern rotational speed. Another possible application is in the detection of a target's position, such as in a proximity detector. One such transducer is shown in U.S. Pat. No. 4,947,035 issued to Zook et al. The conventional features of earlier optical transducers are the use of sensor light propagating through a magneto-optic material in combination with a magnet or other source of a magnetic field such as can be induced by electric current in a conductor. In a magneto-optic material, the polarization state of light propagating through the material is rotated through an angle proportional to the magnetic field. This angular rotation in the light's polarization state results from the effects of an electromagnetic phenomena known as the Faraday Effect. Rotation of the sensor light's angle of polarization is then converted into an amplitude modulation of the light intensity through the use of one or more polarizers. This amplitude modulation of light can then be detected by the use of electro-optic transducers such as photodiodes and similar devices that produce electrical signals proportional to the intensity of incident light thereon.

Because the basic operation of optical transducers utilizing the Faraday Effect depends on amplitude modulated intensity signals, the accuracy of the information contained in the modulated signal is highly dependant on the intensity of the light source, the sensitivity of the light detectors, and changes in light intensity due to variations in the optical elements through which the light travels. Accordingly, prior systems relied on the use of a reference light beam that has a wavelength that is different from the wavelength of the sensor light and typically has a wavelength outside the active bandwidth of the magneto-optic material. By having a reference light beam with a different wavelength from that of the modulated beam, the reference beam can be transmitted along a similar optical path as the modulated beam but is unaffected by the magneto-optic material. The use of this referencing scheme, however, is complicated and expensive because different wavelength light sources are required, special processing of the magneto-optic material can be required, and the sensor itself may need to have secondary optical paths to transmit the reference beam. Also, intensities of the different sources can still change with time and temperature and affect accuracy.

For these and other reasons that will be apparent hereinbelow there exists a need for a debris monitoring system that is both accurate and cost-effective to use and that provides a real-time analysis of the accumulation of magnetic debris in a fluid. There also exists the need for an inherently self-referenced optical sensor that can detect a variable magnetic field with high accuracy as may be used in a proximity detector.

SUMMARY OF THE INVENTION

The present invention departs significantly from the prior art by providing a debris monitoring system that utilizes an optical transducer/sensor rather than the known electric or magnetic chip detectors. The use of an optics-based sensor in accordance with the present invention overcomes the aforementioned drawbacks of the prior art concerning noise induced errors and sensitivity to electromagnetic interference. The debris monitor contemplated by the instant invention operates to accumulate and detect magnetic or ferrous debris in a fluid without the presence of any electronic components in the immediate fluid environment. The sensor operates entirely by the use of magnetics and optics to detect the presence, quantity and rate of accumulation of debris in a fluid. This information concerning the debris is transduced into a modulated characteristic of light that is demodulated by an electronic transducer that can be remote from the environment of the monitored fluid. Thus, the electronics package can be physically located in a remote region that has a substantially reduced background noise and properly conditioned for the operation of temperature sensitive electronic devices.

According to one aspect of the invention, a fluid debris detector is provided that utilizes the Faraday Effect in an optical transducer that detects the accumulation of magnetic debris on a probe. The optical transducer detects the changes in a magnetic field caused by the accumulation of magnetic particles on or near the magnetic field source. The probe that contains the optical transducer can be placed directly in the fluid. The probe contains only the magnetic and optical elements of the overall apparatus, with the electronics portion being located remote from the fluid being monitored. In accordance with the invention, the debris sensor has an inherent memory with respect to the amount of accumulated material on the probe so that the output of the debris monitor is a continual real-time indication of the amount of debris captured from the fluid. This aspect of the invention simplifies computation of the rate of debris accumulation, and also permits any number of such debris monitor probes to be used at the same time during multiplexed data collection without risk of losing or missing important debris accumulation information. Rate of accumulation is derived by differentiating with respect to time the continual real-time quantity data from the probe. The probe detects any particle that is captured within the magnetic field, so that an entire spectrum of particle sizes is sampled.

The instant invention provides a debris monitoring device in which the debris accumulator and the optical transducer can be optimally packaged in a compact probe. According to this aspect of the invention, the entrained debris is removed from the fluid as well as sensed by a single device within the fluid conduit. Because the debris monitoring device provides a constant real-time indication of the amount of entrained debris in the fluid, the probe does not have to be frequently removed for inspection and analysis. Within the probe housing, the magnetic field source can be physically sealed from the optical transducer. Thus, the magnetic field source can be directly exposed to the fluid being monitored to optimize the capture and retention of debris on the probe, while the optical transducer is positioned within the bounds of the applied magnetic field, but is protected from the fluid and debris.

According to another aspect of the invention, a magneto-optic transducer is provided that in combination with an electro-optic transducer is self-referencing to normalize amplitude modulated intensity signals of light thereby making the system insensitive to variations in the electro-optical elements as well as variations in the optical path elements. The self-referencing feature is accomplished by a non-reciprocal bi-directionally addressed probe apparatus and method that self-references using the same amplitude modulated signals that contain the magnetic field variation information. A magneto-optic transducer in accordance with the present invention can be used in any application wherein an event, function, operation or other occurrence provides a mechanism to modulate or change a magnetic field. In particular, in accordance with our invention, we describe herein methods and apparatus for using the magneto-optic transducer invention in a debris monitoring apparatus, and also in a proximity detector.

The present invention also provides a new method for the detection and accumulation of debris with a sensor in a fluid on a real-time basis. According to the invention, the method provides real-time information on the quantity of debris accumulation, as well as the rate of accumulation as calculated from differentiating the direct sensor output. This method involves the use of an optical transducer to detect the accumulation of debris on or near a magnetic field source. The optical transducer is used to detect the variation in the applied magnetic field caused by accumulation of debris near the magnet, convert the magnetic field variation to a change in angular rotation of a polarized light source, further converting the rotated angle of polarization into a variation in intensity of the light, and detecting the modulated light intensity with an electro-optic transducer to detect debris in the fluid.

The present invention also provides a new method for detecting variations in a magnetic field with the use of a magneto-optic material that exhibits the Faraday Effect. This method involves placing the magneto-optic material within the bounds of the variable magnetic field, and bi-directionally addressing or interrogating the material with linearly polarized light, using the Faraday Effect induced through the magneto-optic material to rotate the light angle of polarization, converting the polarization angle rotation to a change in the light intensity, and using a light intensity detector to convert the modulated light intensity into signals representative of the variable magnetic field. In accordance with the invention, the bi-directional interrogation is performed through a non-reciprocal optical sensor, which in combination with the use of an electro-optic transducer and a ratio signal processing technique, provides self-referencing using the same detection signals that contain the magnetic field variation data. This method eliminates variations in the optical sensor output due to causes other than the effects from the magnetic field variations induced through the magneto-optic material. A ratio such as a preferred difference-over-sum processing technique also provides an inherent self-diagnosing function that permits simple implementation of a built-in-test feature that checks proper operation of the debris detector. This method is described herein as useful in a method for detecting entrained debris in a fluid, and a method for proximity detection, though other applications will be apparent to those skilled in the art.

These and other aspects and advantages of the present invention will be apparent to those skilled in the art from the following detailed description of the preferred embodiments in view of the accompanying drawings.

DESCRIPTION OF THE PREFERRED AND ALTERNATIVE EMBODIMENTS

A. Preferred Embodiment for a Debris Monitor

Figure 1:
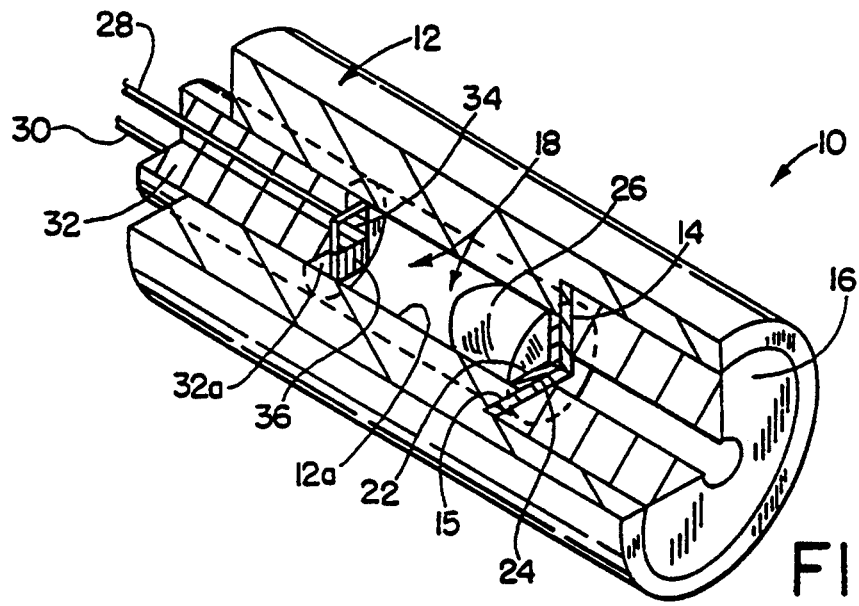
FIG. 1 is a schematic representation in partial section of a magnetic fluid debris monitor probe and optical sensor according to the present invention.

With reference to FIG. 1, a debris monitoring system according to the present invention for detecting and accumulating magnetic debris entrained in a fluid includes a magnetic probe 10 that is constructed to be fluid tight so that the probe 10 can be immersed in the fluid being monitored, such as, for example, the oil scavenge line in a gas turbine engine (not shown). While the particular application of the invention is explained herein with reference to detecting particles in an engine lubricating fluid, this is only for purposes of explanation. Those skilled in the art will readily appreciate that the debris monitor system can be adapted to any fluid system wherein there is a need to monitor and accumulate magnetic particulate debris and contamination. Moreover, with respect to the optical sensor apparatus and method contemplated by the present invention, those skilled in the art will understand that these aspects of the invention can be used in many types of sensor and detector applications wherein the advantages of using magneto-optic transducers are available such as, for example, a proximity detector.

The probe 10 includes a housing 12 made from a suitable material such as non-magnetic stainless steel so as to be leakproof and not susceptible to degradation from the fluid into which the probe 10 is placed. The housing 12 is generally cylindrical in shape and includes an inner partition 14 which may be conveniently seated on a shoulder near one end of the housing. The shoulder 15 may be formed during a machining process used to form the inner radius 12a of the housing 12. Of course, housing 12 can also simply be formed from a piece of stainless steel tubing.

The partition 14 divides the probe 10 into two axially aligned chambers. One chamber is used to hold a ring magnet 16 that is appropriately sized to slide into the housing 12 and seat against the partition 14. The other housing chamber slidably receives and retains an optical sensor assembly 18. The optical sensor assembly 18 is separated from the magnet 16 as well as sealed from the external environment around the probe 10 by a diaphragm or other suitable sealing device (not shown) between the partition 14 and the shoulder 15. The magnet, however, may conveniently be exposed directly to the fluid in situations where such exposure will not cause deterioration of the magnet over time. The magnet attracts magnetic particles suspended in the fluid, which attach either directly to the magnet or to the exterior surface of the housing near the magnet. In order to optimize capture of particulate debris, the probe is usually placed in the fluid line parallel to the fluid flow such as with the magnet facing upstream so that the fluid flows directly against the magnet's exterior face.

The optical sensor assembly 18 includes a magneto-optic transducer 22, preferably in the form of a piece of magneto-optic material that exhibits the Faraday Effect when placed within the bounds of a magnetic field. As will be fully explained hereinafter, a magneto-optic material exhibits the Faraday Effect in relation to the strength and alignment of a surrounding magnetic field, the length of the magneto-optic material that light travels therethrough, and the Verdet constant, which is a material constant determined by the type of magneto-optic material selected. As used herein, the term "light" is used in its broadest sense and refers to any electromagnetic energy or radiation within an optical bandwidth defined by the material selected for the magneto-optic transducer.

The optical sensor assembly 18 further includes a light-reflective element 24, such as a mirror. The mirror 24 can be a separate element from the transducer 22, or preferably can be directly affixed to or deposited on the back surface of the magneto-optic material. A collimating lens 26 is placed adjacent the other surface of the magneto-optic material opposite the mirror 24. The focal length of the lens is selected so as to focus incoming light on the reflective surface of the mirror 24.

A pair of optical fibers 28,30 are mounted and held in a ferrule 32 that is sized to slide into the housing 12. The optical fibers 28,30 terminate at an inner surface 32a of the ferrule. A pair of linear polarizers 34,36 are mounted on the inner surface 32a of the ferrule adjacent the optic fibers 28,30 in such a manner that light traveling through the first optic fiber 28 passes through the first polarizer 34; and light traveling through the second optic fiber 30 passes through the second polarizer 36. That is, the first optic fiber 28 is optically aligned with the first polarizer 34, and the second optic fiber 30 is optically aligned with the second polarizer 36.

A second suitable sealing device (not shown) such as an O-ring is used to ensure a hermetic seal for the optical sensor assembly 18 so that the probe 10 can be fully immersed in the monitored fluid without fluid leakage into the housing 12.

As explained herein, the probe 10 is placed in the fluid to be monitored (not shown). As illustrated in FIG. 1, the only elements that are present in the high temperature and hostile environment of the fluid are optical and magnetic elements. The fiber optics will provide the "communication link" the signal processing electronics which can be located remote from the optical sensor 18 to reduce the effects of noise and temperature.

Figure 2:
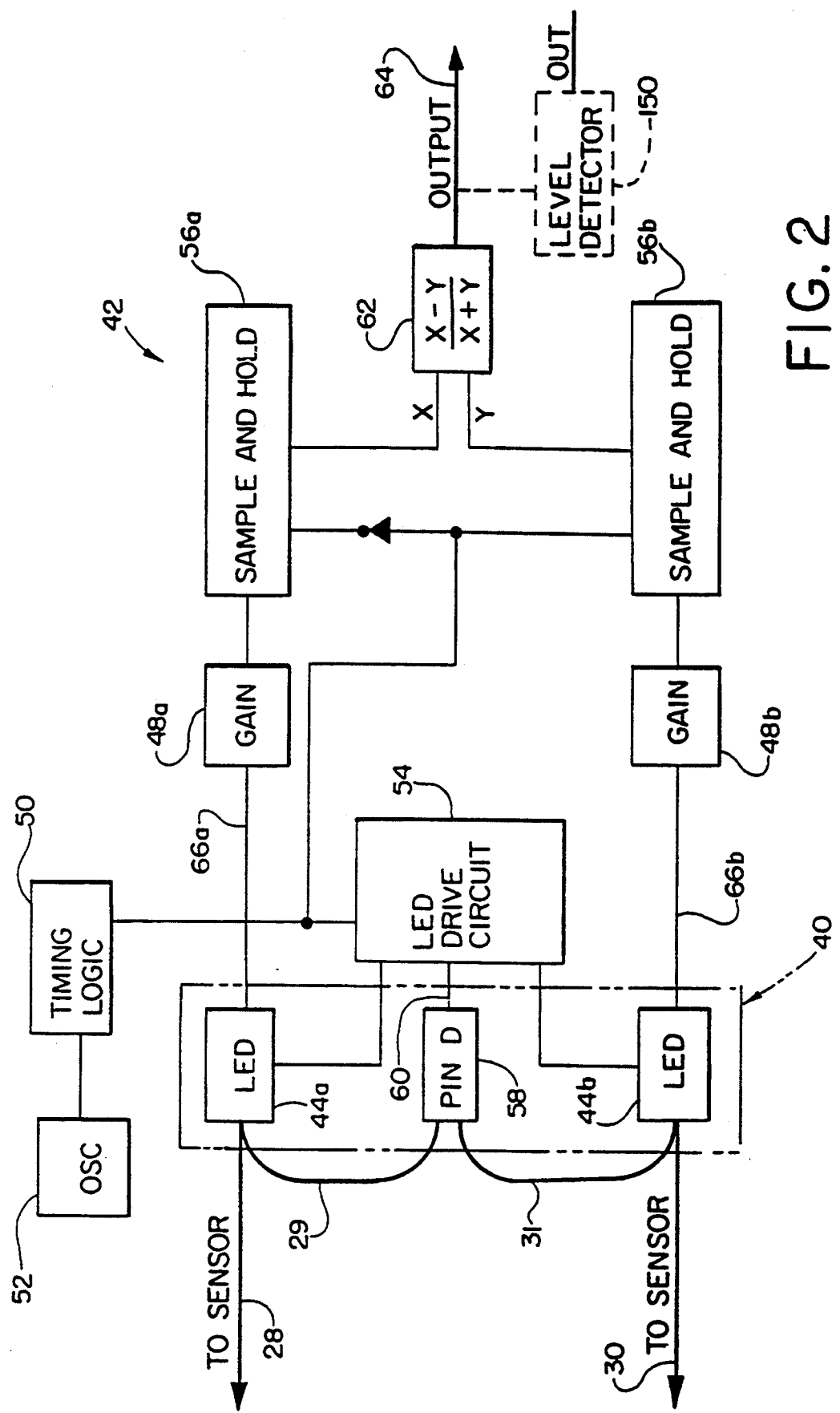
FIG. 2 is an electrical schematic diagram of an electro-optic transducer and signal processing circuit according to the present invention suitable for use with the debris monitor probe and optical sensor shown in FIG. 1.

An electro-optic transducer 40 and signal processing circuit 42 is schematically represented in FIG. 2. The electro-optic transducer 40 includes one or more light sources 44. The number of light sources used will depend on the particular configuration of the interrogation scheme implemented, as will be more fully explained hereinafter. However, in accordance with the present invention, it is important to note that all the light sources preferably emit light of similar bandwidth and wavelength. There is no need to use light sources of different wavelengths. Preferably, the light sources are generally matched in terms of output wavelength and intensity, however, perfect matching is not required as the overall system is self-referencing to compensate for such variations.

The electro-optic transducer 40 also preferably includes at least two light detectors 46. In the preferred embodiment represented in FIG. 2, the same electronic device acts as both a source of light 44 and a light detector 46. Such a device could be, for example, a light emitting diode. In other embodiments that will be described hereinafter, there is provided a light detector 46 for each respective light source 44. Alternatively, when only one light source is used in common for both optic fibers 28,30, two detectors are still used, one for each of the respective fibers. It is also possible, with the use of an optical switch, to use only a single source and detector.

The light detectors 46 produce analog electrical signals that are directly proportional to the intensity of incident light thereon. These low-amplitude analog signals are amplified by controlled-gain amplifiers 48. The remaining circuitry in the signal processing circuit 42 converts the amplified analog detector output signals into useful data representing the debris detected by the probe 10, as will be further explained hereinbelow.

B. General Principles of Operation

One of the underlying concepts of the present invention is the application of the Faraday Effect for use in a fluid debris detector or a proximity detector. Briefly, the Faraday Effect is a phenomenon of light propagation. When light passes through a Faraday Effect material, the radiation plane of polarization is rotated when a magnetic field is aligned with the direction of propagation of the light. The rotation angle, or more precisely the degree of rotation, is a function of the magnetic field in the region of the material, the material or Verdet constant, and the length of the material through which the light travels. Different materials exhibit the Faraday Effect to a greater or lesser degree than other materials. As used herein the term "magneto-optic material" is a generic reference to any material that adequately exhibits the Faraday Effect for use in a magneto-optic sensor. Magneto-optic materials best suited for sensor applications wherein there is a need to detect slight or gradual variations in a magnetic field are rare earth garnet films grown by liquid phase epitaxy (LPE), which have been doped with elements that increase Faraday rotation and decrease optical absorption in the infrared region of the radiation frequency spectrum. These materials have very high Faraday rotation characteristics and a transmission window in the wavelength region of approximately 800 nm. However, other materials may also be suitable, such as yttrium iron garnet and various Faraday glasses.

Certain other factors are important in choosing a magneto-optic material for use in a debris sensor. The magnetic field needed to produce a modulated polarization angle of light should be low enough so that small sized particles and low mass of debris accumulating near the magnet produce detectable changes in the overall debris sensor output signal. That is, a small change in magnetic field characteristics should produce a detectable change in the polarization angle of the light passing through the magneto-optic material. The angle through which polarized light is rotated when it passes through the transducer should vary monotonically with respect to the applied magnetic field. Also, the material properties should be stable over a wide operating temperature range. A magneto-optic material whose compensation temperature is less than the sensor's minimum operating temperature range and whose Curie temperature is greater than the sensor's maximum operating temperature must be used. A particular material that has been found to be suitable for use in a debris detector in accordance with the present invention is MGG-A78 made by Mitsubishi Gas Chemical Company, Inc.

With further reference to FIG. 1, one of the significant features of the instant invention is that the probe 10 elements define a single optical path for light transmitted therein and a single wavelength of light is preferably used, yet the device is fully self-referenced. The self-referenced aspect of the invention compensates for losses and other variances in the optical path that can affect the intensity of the interrogation light transmitted through the optical sensor other than intensity changes caused by variations in the applied magnetic field.

Generally, light is emitted from one of the light sources 44 and is optically coupled through the first optical fiber 28 to the input polarizer 34. Linearly polarized light exits from the polarizer (with some attendant decrease in light intensity) and enters the lens 26. The polarized light is characterized by having a specific angle of polarization that is determined by the angular orientation of the polarizer 34. The lens 26 focuses the light along an optical path through the magneto-optic material 22 to the light-reflective element 24. The light is reflected back through the magneto-optic material 22, enters the second polarizer 36 which acts as an analyzer, and enters into the second optical fiber 30. The optical fiber 30 couples the reflected light back to the electro-optic transducer 40. The electro-optic transducer then converts the reflected light intensity to an analog electrical signal for further processing as explained hereinbefore.

When the linearly polarized light first passes through the magneto-optic transducer material 22, the light's angle of polarization is rotated under the influence of the magnetic field from the magnet 16 in accordance with the Faraday Effect. When the reflected light passes through the magneto-optic transducer, the angle of polarization is again rotated the same amount and in the same polar direction. In other words, the transmitted light undergoes a double rotation. The rotation of the angle of polarization is cumulative because magneto-optic materials are reciprocal. By reciprocal is meant that characteristic of magneto-optic materials by which the angle of rotation and the polarity of rotation is independent of the direction that light propagates through the magneto-optic material 22.

The second polarizer 36 also has an associated angle of polarization for the reflected light that passes therethrough. The polarization angle of the polarizer 36 is intentionally chosen to be different from the angular orientation of the input polarizer 34. This offset is used to detect the rotation caused by the magnetic field and, in combination with the reciprocal magneto-optic material, to provide the self-referencing feature of the instant invention.

The light sources 44 that transmit light to the optical fibers 28,30 are alternately actuated. In other words, light is transmitted through the probe 10 in a bi-directional mode. Thus, when light is input to the first optical fiber 28, the second optical fiber is used as the output fiber. Conversely, when light is transmitted to the second optical fiber 30, it passes through the second polarizer 36 which now acts as the input polarizer, then through the lens and magneto-optic material 22, gets reflected back by the mirror 24 through the magneto-optic material 22 and through the first polarizer 34 (which now acts as the analyzer) and out through the first optical fiber 28 to the electro-optical transducer for further processing. Thus, the designations of "first" and "second" and "output" and "input" fibers and polarizers herein is simply for ease of explanation. In fact, there is but one optical path through the probe 10 and that path is bi-directionally addressed and is defined by the position of the fibers relative to the center axis of the lens 26, the focal point of the lens itself, and the reflection angle of the mirror 24. The arrangement by which light is reflected back through the magneto-optic material may be referred to as a "folded" optical path.

The light is transmitted through the polarizers bi-directionally by arranging the optical fibers off center from the central axis of the lens. The off-center alignment of the fibers has the added benefit of substantially reducing the amount of unmodulated reflected and backscatter light coupled from the lens and magneto-optic material into the output fibers. The optical sensor 18, therefore, produces a low background optical noise level. Furthermore, because the magneto-optic material is reciprocal and the polarizers are oriented at different angular displacements with respect to each other, the optical path through the probe 10 is non-reciprocal. This important aspect of the invention permits not only the self-referencing feature but also a built in test to verify the optical path integrity, as will be more fully explained hereinafter.

C. Detailed Explanation of Operation of a Debris Monitor

The preferred embodiment of a debris monitor system according to the present invention is schematically represented in FIGS. 1 and 2. The probe 10 functions as an magneto-optic transducer that converts magnetic field intensity or strength into a corresponding intensity of light. The electronic system of FIG. 2 controls optical actuation of the probe 10 and converts the modulated light intensity into data representing the state of debris accumulation on the probe 10. By interrogating the probe 10 in a bi-directional manner, the debris monitor system is self-referencing and functions with an inherent built-in-test capability.

In operation, a timing control circuit 50 is used to control energization of the light sources 44a and 44b. An oscillator 52 inputs the primary clock pulses for the timing control circuit 50; and the timing circuit 50 generates output signals that control both the light source driver circuit 54 and the data sample and hold circuits 56a,b. All of the electronic components used in the circuit of FIG. 2 are well-known and commercially available; and implementing the circuit of FIG. 2 is readily achievable from any number of circuit design books available from component manufacturers. Of course, the circuit of FIG. 2 can be built up from discreet components or arranged onto a single integrated circuit, or a combination thereof.

The timing control circuit 50 operates to actuate alternately the light sources 44a,b. Actuation of the light sources 44 is mutually exclusive such that when one light is on, the other is necessarily off. Also, when one of the LEDs is acting as a source, the other is acting as a detector for the light transmitted through the optical sensor 18, and vice-versa. Preferably, the light sources 44 are light emitting diodes (LEDs) such as part number TOX-9008 manufactured by Texas Optoelectronics, Inc. Use of light emitting diodes is preferred because the LED can serve as both a source of light and a detector of light. An LED, when exposed to incident light of its own wavelength, generates an analog electrical signal that is directly proportional to the intensity of the light incident thereon.

In a complementary manner, the timing circuit 50 also controls the sample and hold circuits 56a,b. The sample and hold circuits are used as temporary memory devices that when enabled sample the analog level of the corresponding LED output and hold that value until it is again enabled to take the next sample. Thus, the timing circuit 50 only enables one of the sample and hold circuits at a time, and only when its corresponding LED device 44 is serving as a detector and not a source. During the periods when an LED is enabled as a source, the corresponding sample and hold circuit is disabled from reading any output signal therefrom.

As with any light emitting source, all LEDs do not emit the same light intensity though readings may be very close. Since operation of the debris monitor system depends in part on detecting light intensity variations, any difference or change in the intensity of the emitted light between the two sources 44 could lead to false readings. One way to obviate this problem is to use only a single source in combination with an optical switch, as will be further explained hereinafter.

Preferably, however, two light sources that emit light at approximately the same wavelength are used. Small variations between the wavelengths emitted are not critical because each LED will by definition detect its own emitted wavelength. The only condition being, of course, that both LEDs emit a wavelength within the active response spectra of the magneto-optic material 22.

A PIN diode 58 or equivalent device is used to regulate the output intensity of the sources 44. As represented in FIG. 2, each LED emits light into its corresponding optical fiber 28,30. By fixing two optical fibers into an optical connector and mating the connector with the LED, one fiber 28 can be used to transmit interrogation light to the sensor 10 and the other fiber 29 can be used to input light to the PIN diode 58 which converts the output intensity into an electrical output signal 60. A similar arrangement is used on the second LED. The PIN diode output 60 is used as a feedback control signal to the LED driver circuit 54. The LED driver 54 automatically adjusts the drive voltage applied to the LEDs to maintain a constant predetermined emitted intensity of light therefrom.

As stated herein, each LED light source 44a,b is optically coupled to a respective one of the optical fibers 28,30. When one of the LEDs is energized, it emits light of predetermined intensity into the corresponding fiber 28,30 which in turn is optically coupled to its corresponding polarizer 34,36. This is referred to herein as "actuating" the light source and its corresponding polarizer.

In accordance with the present invention, the debris monitor system uses the magnet 16 to capture and retain magnetic particles in the monitored fluid. The same magnet is also used to establish a magnetic field with a portion of this field passing through the magneto-optical transducer material 22 with a predetermined orientation thereto. The magnet 16 maintains a constant magnetic field that is unperturbed, but for the accumulation of particulate debris thereon. As magnetic particles adhere to the exposed face of the magnet, or to the probe housing 12 near the magnet, the magnitude of the field through the magneto-optical material 22 changes, and eventually can change polarity. The magnetic field changes as a result of the total mass of particles captured and remains in its new state until more particles are captured. This results in two of the more significant benefits of the present invention. First, the probe 10, when the magnet 16 captures the particulate debris, has an inherent memory in the form of the altered magnetic field. This altered field at every instant of time provides a real-time indication of the amount of particulate debris on the probe 10. Second, the magnetic field varies as a function of the total mass so that the detection capability of the probe 10 is not limited to particles having a minimum size. Of course, the magnet captures debris so that if desired the usual visual and laboratory analysis of the debris can also be performed.

The debris monitor system, in accordance with this invention, detects changes in magnetic field by optical interrogation of the magneto-optic material 22 with linearly polarized light. Because the degree of rotation in the polarization angle of light traveling through the magneto-optic material is a function of the magnetic field, changes in the magnetic field cause corresponding changes in the light polarization angle. The debris monitor system detects the rotation angle induced by the magneto-optic material and interprets that change as an indication of the altered magnetic field, and hence accumulation of particles on the probe 10.

The preferred way to detect the angle of rotation is the use of two polarizers that have different polarization angles with respect to each other. The first polarizer 34 preferably has a polarization angle that is 45 degrees rotated from the polarization angle of the second polarizer 36. The preferred differential of 45 degrees is chosen because, by definition, the intensity of light that has passed once through each polarizer 34,36 and the magneto-optic material is defined by the equation:

$$I = \tfrac{1}{2} I_o [COS^2(\theta p + HLV)] \qquad (1)$$

where I is the exit intensity through the second or analyzer polarizer, Io is the input intensity, H is the applied magnetic field, L is the optical path length through the magneto-optic material 22, V is the Verdet material constant, and $\theta p$ is the relative angle of polarization between the two polarizers 34,36, namely 45 degrees. From equation (1) it is apparent that 45 degrees is an optimal angle since $COS^2(45 \text{ degrees}) = \tfrac{1}{2}$. The sign of $\theta p$ will be plus (+) or minus (−) depending upon which polarizer is the input polarizer and which serves as the analyzer. Because the direction of propagation is alternated, each polarizer acts as the analyzer every other actuation.

Figure 3A:
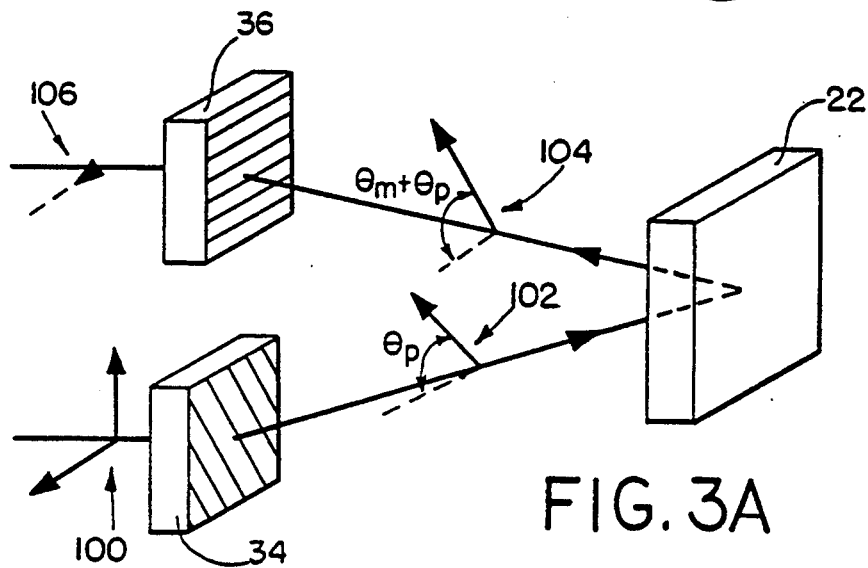
FIGS. 3a and 3b are simplified schematics of the polarization elements of a non-reciprocal optical transducer in accordance with the present invention.

FIG. 3 represents in a simplified manner how the optical sensor assembly 18 transduces the magnetic field through the magneto-optic material into a modulated intensity of the transmitted light. In one-half of an interrogation cycle, FIG. 3a, light 100 emitted from the source 44a is coupled by the associated optical fiber 28 to pass through the input polarizer 34. The light 102 that exits the input polarizer has an angle of polarization determined by the rotational alignment of the polarizer material. The intensity of the polarized light 102 exiting the input polarizer 34 will, of course, be reduced as compared to the input intensity to the polarizer.

The linearly polarized light 102 is focused by the lens 26 (not shown in FIG. 3) to pass through the magneto-optic material 22 along an optical path that is generally parallel to the applied magnetic field portion that passes therethrough. The light is then reflected by the mirror 24 and passes again through the magneto-optic material 22. The reflected light 104 that exits the magneto-optic material 22 now has an angle of polarization $\theta p + \theta m$ that has been rotated by an angle $\theta m$ from the input polarization angle $\theta p$ in relation to the magnitude of the magnetic field through the magneto-optic material 22. More specifically, the angle $\theta m$ is a function of twice the angle of rotation caused by one pass through the magneto-optic material because the light has passed through the reciprocal magneto-optic material twice. The reflected light 104 again passes through the lens 26 and into the analyzer polarizer 36. The reflected light 106 that exits the second polarizer 36 will have an intensity determined by the 45 degree differential between the polarizers and the degree of rotation $\theta m$.

If we assume for the moment, for purposes of explanation, that the magnetic field through the material 22 is zero, then $\theta m = 0$ and the intensity of the exit light 106 will strictly be a function of the offset angle of polarization between the two polarizers 34,36 and any other losses inherent along the optical path. The zero gauss magnetic field can be thought of in a sense as establishing the DC or steady state intensity level of the interrogating light. Therefore, any rotation $\theta m$ added to the polarization angle caused by an applied magnetic field will cause a corresponding change in the intensity of the light 106 exiting the analyzer polarizer.

Figure 3B:
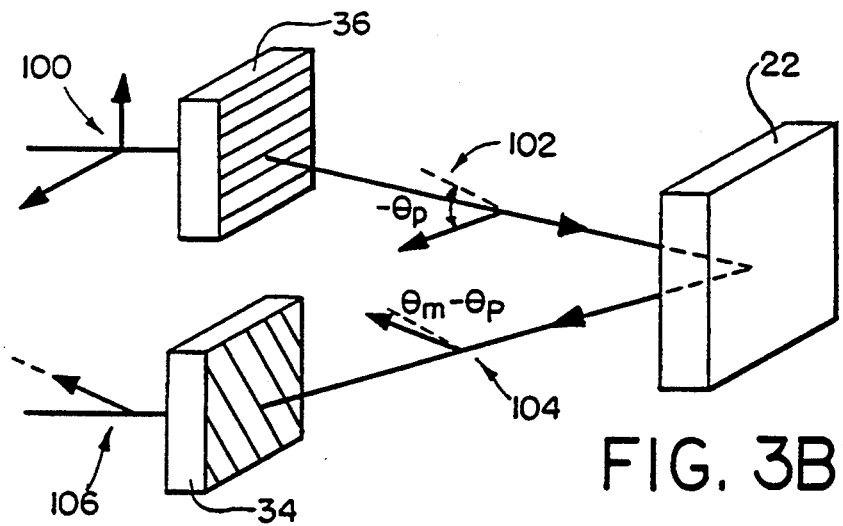

In accordance with the present invention, during the other half of an interrogation cycle as represented in FIG. 3b, the direction of the propagation of light is reversed. Light is passed into the input polarizer 36 from the input optic fiber 30, passes twice through the magneto-optic material 22 along the same optical path, and exits through the analyzer polarizer 34 into the other optic fiber 28. Again, if we assume zero magnetic field, the intensity of the light exiting the analyzer 106 will be equal to the intensity of the light that traveled the opposite direction at zero magnetic field. Also, in both cases, $\theta m$ has the same magnitude and polarity because the magneto-optic material is reciprocal. However, $\theta p$, or the angular difference between the two polarizers will now be of opposite polarity because the light has traveled the reverse direction therethrough. Thus, if we refer to $\theta p$ as the differential angle during the first half of an interrogation cycle, then during the second half the differential angle is $-\theta p$.

It is now apparent why the optical sensor assembly 18 is referred to as being non-reciprocal. It is non-reciprocal because the angle of rotation caused by the magneto-optic material is independent of the direction of propagation, and thus the intensity change of light propagating through the offset polarizers along the optical path depends on the direction of the propagation. Therefore, a ratio defined by the difference over sum calculation of the two exit light intensities for one interrogation cycle yields an output that normalizes all intensity losses not caused by the Faraday rotation (because the interrogation light during both halves of the cycle has traveled the exact same optical path), and results in a value that is only a function of that rotation. Those skilled in the art will appreciate that ratios other than a difference-over-sum calculation can provide useful information. For example, a simple ratio of the two detector outputs still provides a normalized signal. The important point is to use two outputs from light samples that traveled bi-directionally along the optical path. The difference-over-sum ratio is preferred in part because it contains an inherent built-in-test capability.

Note, for example, what happens if $\theta m$ is 22.5 degrees. The double pass of light through the magneto-optic material 22 results in a total 45 degree rotation. Since the polarizers are offset 45 degrees with respect to each other, then a certain amount of light will pass through in one direction of propagation (during one half of an interrogation cycle) while almost no light will pass through in the opposite direction of propagation (during the other half of one interrogation cycle). Thus, the addressed bi-directionally optical path according to the present invention is truly non-reciprocal, and in fact, inverse.

During each interrogation sequence, the reflected light that exits the analyzer polarizer is coupled by the respective optic fiber 28,30 back to the corresponding light detector device 46a,b. In the preferred embodiment, the detector is the same as the deactivated source 44a,b. The detector device produces an electrical output signal 66 that is proportional to the intensity of the incident light thereon.

By using the sample and hold circuits, the difference over sum ratio of each successive pair of interrogation light samples is calculated by a ratio circuit 62. The ratio circuit 62 can be realized in any number of ways that are well known to those skilled in the art.

Figure 4:
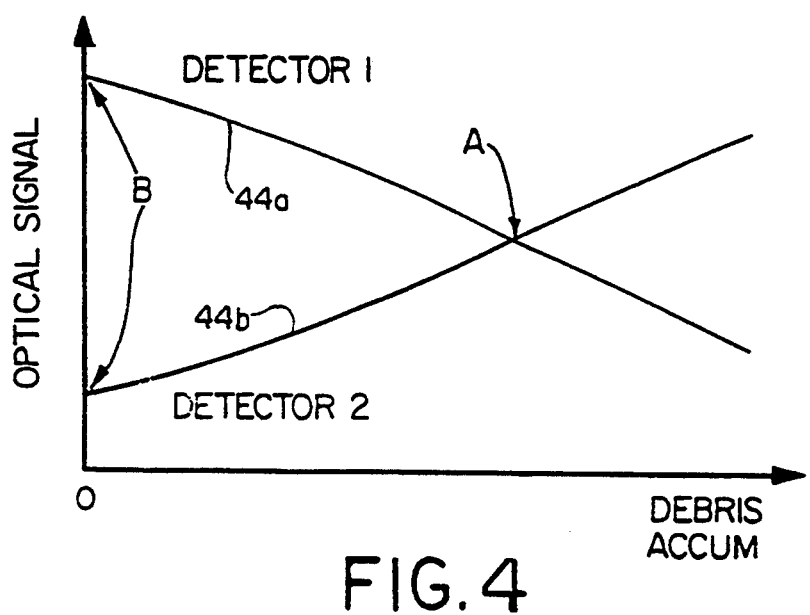
FIG. 4 is a graphical representation of detector output signals versus debris accumulation for the debris monitor shown in FIGS. 1 and 2.

FIG. 4 represents a typical expected relationship that exists between the output signal of the detectors and accumulation of debris on the probe 10. The Y-axis charts light intensity sensed by a detector 44 and the X-axis charts quantity of debris. Using the X-axis to chart debris accumulation is the same as saying it charts changing magnetic field since the two are directly related. Because the optical sensor 18 is non-reciprocal, the output readings from the light detectors 44a,b act inversely to each other. That is, as the amount of debris increases the intensity of light detected by one of the detectors will decrease proportionally, while the other will increase proportionally. At point A designated in FIG. 4, the detector readings are equal. As explained hereinbefore, point A occurs when the magnetic field through the magneto-optic material 22 is zero.

Figure 5:
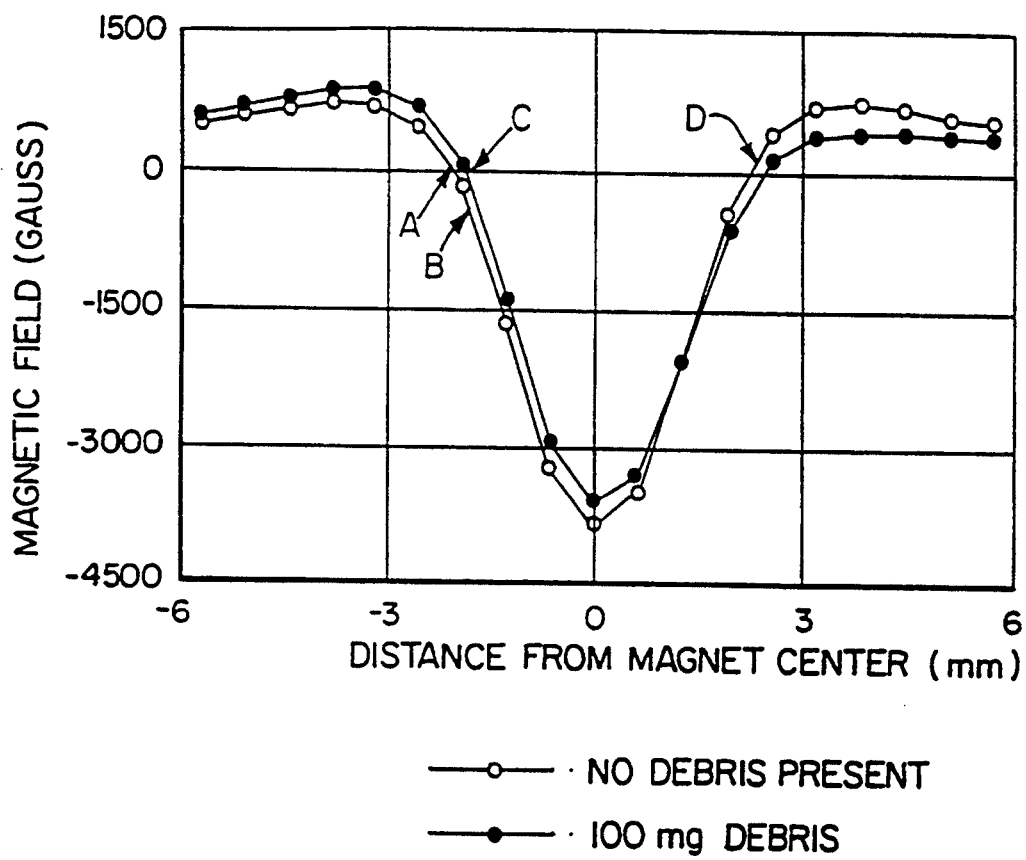
FIG. 5 is a graphical representation of axial magnetic field versus distance of a ring magnet for conditions of no debris accumulation and with debris accumulation.

FIG. 5 represents a typical expected axial field of a ring magnet 16 versus position from the center of the magnet, with and without ferrous debris attached to the front of the magnet. The axial field is the field of interest since the optical path of light through the magneto-optic material can be easily aligned in a predetermined manner to be parallel to the axial field in order for the Faraday Effect to be manifested. As represented in FIG. 5, when ferrous particles are present on the magnet's face, the magnetic field is modulated such that the magnitude of the field at any given point along the axis of the magnet is changed. Specifically, as debris accumulates, the response curve shifts. Thus, the two nodes, or positions of zero magnetic field, shift towards the face of the magnet on which debris accumulates.

Change in the magnetic field is greatest at positions closest to the face of the magnet collecting debris, and decreases for positions further away from the face. Although the ideal position for the magneto-optic material in terms of magnetic field change is in front of the node closest to the magnet face collecting debris, as a practical matter, it is easier to mount the magneto-optic material just behind the magnet as represented in FIG. 1. This simplifies sealing the optical elements from fluid and debris. Even with this preferred configuration, the magneto-optic material can be easily positioned near one of the magnet's node.

One of the nodes is identified by point A in FIG. 5. The magneto-optic material can thus be positioned, for example, at point B. As debris accumulates, the node A moves towards the magnet's center, causing a significant change in the magnetic field passing through the magneto-optic material that is at a position corresponding to point B. In fact, after enough material accumulates, the zero field condition designated by point C will occur in the material 22.

Because the optical intensity of the bi-directionally interrogating light is ultimately a function of the magnetic field through the magneto-optic material, the intensity will change as debris accumulates. By choosing a magneto-optic film which rotates the polarization state of light through an angle that is dependent on the magnetic field, the amount of debris residing on the probe 10 can be determined from the light detector output signals.

With the magneto-optic material positioned at, for example, a location corresponding to point B in FIG. 5, the detector outputs will be approximately represented by point B on FIG. 4 when no debris is present on the magnet. As debris accumulates, the intensities detected by the two detectors change inversely with respect to each other. As the magnetic node passes through the magneto-optic material, the difference over sum calculation gives zero as represented at point A on FIG. 4. As debris continues to accumulate the difference over sum calculation will result in a reverse polarity again due to the inverse relationship of the detector outputs. FIG. 5 also illustrates how the preferred position of the magneto-optic material is in the magnetic field region that is generally linear between the node and the magnet's center.

Table I shows how the collection of magnetic debris affects the field of a ring magnet. It has been discovered that the dimensions of the ring magnet are important in choosing a magnet for a debris monitor. A ring magnet can be described as the superposition of two oppositely poled cylindrical magnets with appropriate dimensions. For a ring magnet, debris will primarily accumulate on the outer portion (large diameter) of the magnet. Therefore, the effects of debris will be detectable most easily when the field of the ring magnet is strongly dominated by the larger diameter. The contribution of the larger outer diameter will dominate when it is at least twice the inner (smaller) diameter of the magnet.

TABLE I

| Iron Filings (Mg) | Field (Gauss) |
| --- | --- |
| 0 | 79.4 |
| 8 | 67.9 |
| 16 | 55.7 |
| 20 | 49.4 |
| 30 | 29.0 |
| 45 | 22.1 |
| 60 | −19.6 |

Figure 6:
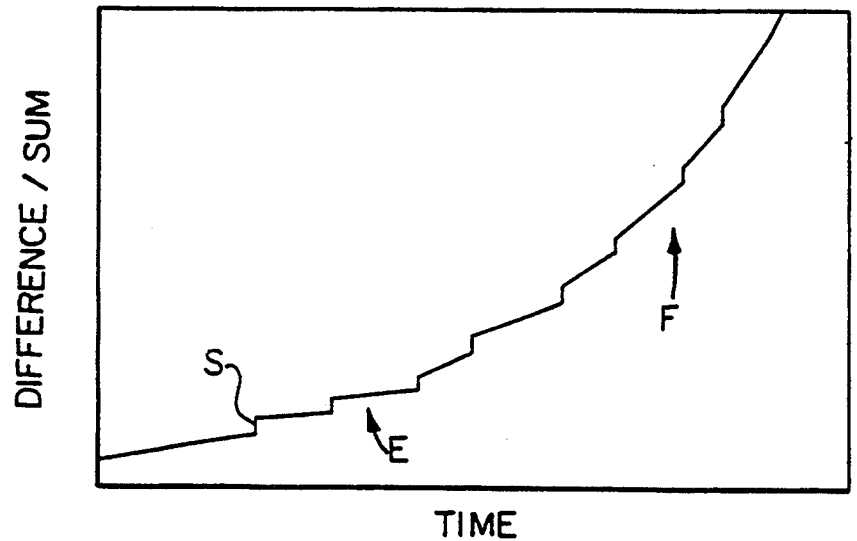
FIG. 6 is a graphical representation of a typical difference over sum ratio versus time for the debris monitor illustrated in FIGS. 1 and 2.

As debris collects on the face of the probe 10 magnet, the optical intensities produced by the bi-directionally addressed optical sensor 18 will change both as a function of quantity and rate of accumulation. The difference-over-sum signal processing provides a self-referenced output having a slope that over time varies as a function of the rate of debris production. Thus, the output signal 64 can be used for trend analysis of the particulate production rate. FIG. 6 represents a typical expected difference-over-sum output signal over time as the rate of accumulation increases. The analog output signal 64 from the difference-over-sum circuit 62 will increase at a gradual generally constant slope E during initial moderate accumulation. This type accumulation might occur, for example, during normal operation of a gas turbine engine. A large debris particle striking the probe 10 would be manifested in a small sharp step in the signal such as at point S in FIG. 6. Then, just before the onset of an engine part failure, the quantity and rate of accumulation will increase, as indicated by the increased slope F of the signal represented in FIG. 6.

Figure 7:
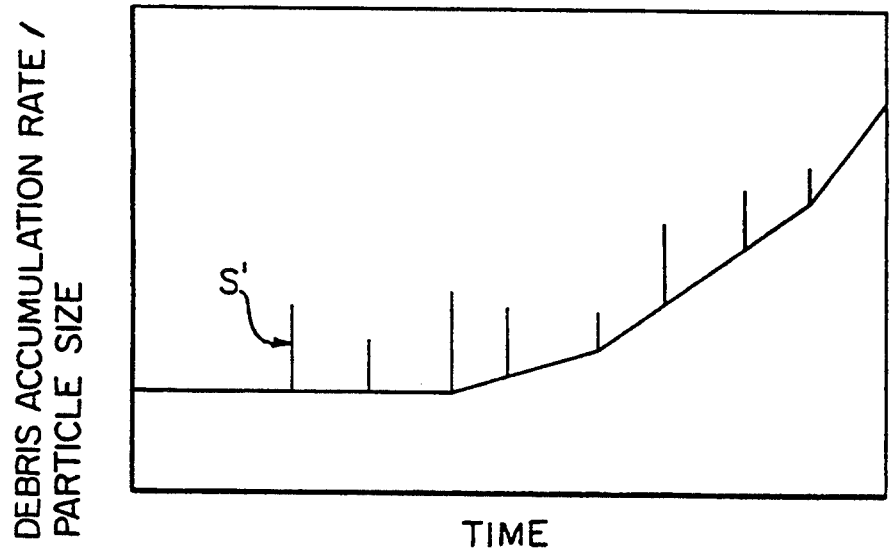
FIG. 7 is a graphical representation of a differentiated values with respect to time of the data represented in FIG. 6.

Increased production of larger particles may or may not accompany a part failure. FIG. 7 shows the differentiated analog difference-over-sum signal output 64 with respect to time. For normal debris production rates, (period E in FIG. 6), the differentiated signal remains constant because the rate of increase is fairly constant, with occasional spikes S' indicating that a larger particle was captured by the probe 10 (corresponding to the step signal S in FIG. 6). When, for example, an engine part begins to fail, as during period F in FIG. 6, debris production rate increases and the differentiated signal is no longer constant. Increased production of particles is manifested in the increased number and closer spacing of the spikes in FIG. 7. However, an important advantage of the present invention is that the rate of accumulation is detected in a real-time manner even if larger particles are not generated, because the debris monitor contemplated by the present invention provides a continual output indicative of the total mass accumulated on the probe 10.

In accordance with the present invention, the difference-over-sum calculation also provides an inherent built-in-test for the debris monitor system. If a failure occurs anywhere along the optical path, or in the detector circuitry, one or both of the detector output signals 66 will be zero. Therefore, a difference-over-sum output signal of plus (+) or minus (−) 1 indicates a failure.

Adjustment of the position of the magneto-optic transducer material 22 near the node of the magnet 16 is simplified by the fact that the ratio signal output 64 goes to zero when the magneto-optic material is at the node.

Because the ratio circuit 62 provides a real-time continual indication of the accumulated debris (updated after each interrogation cycle), the debris monitor contemplated by the invention is especially suited for applications that require use of multiple detectors. (For example, a multi-engine aircraft with multiple oil scavenge lines). This is because the real-time debris accumulation data 64 can be accessed with known data multiplexing techniques without risk of missing potentially critical debris accumulation information.

The present invention also contemplates the methods described hereinabove in the explanation of the debris monitor system for detecting quantity and rate of accumulation of debris on the magnetic probe 10 using bi-directional non-reciprocal optical interrogation of a magneto-optic material. The invention further contemplates the methods described hereinabove in the explanation of the optical sensor apparatus of using a bi-directional non-reciprocal self-referencing optical interrogation to detect the intensity of a target magnetic field.

D. Alternative Embodiments of the Debris Monitor

Figure 8:
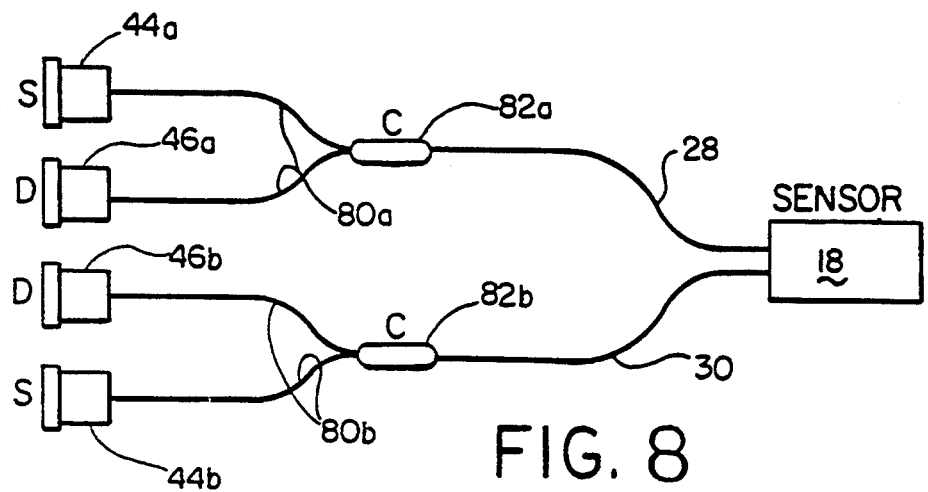
FIGS. 8–10 are simplified schematic illustrations for light source and detector arrangements for a debris monitor according to the present invention.
Figure 9:
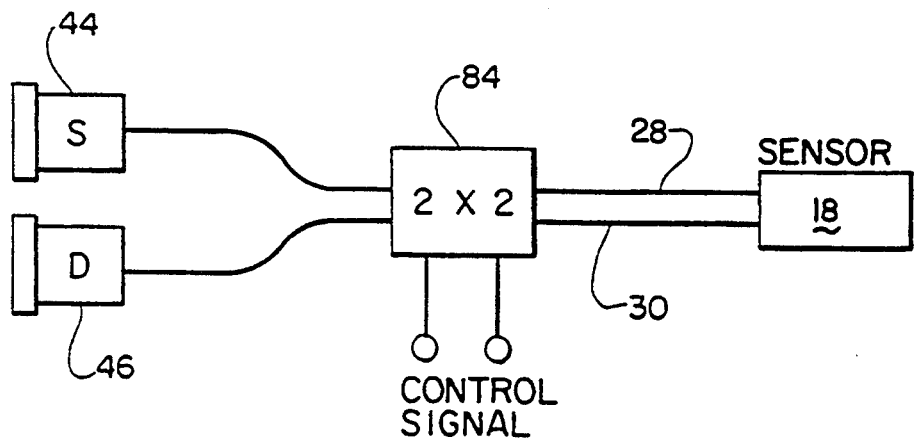
Figure 10:
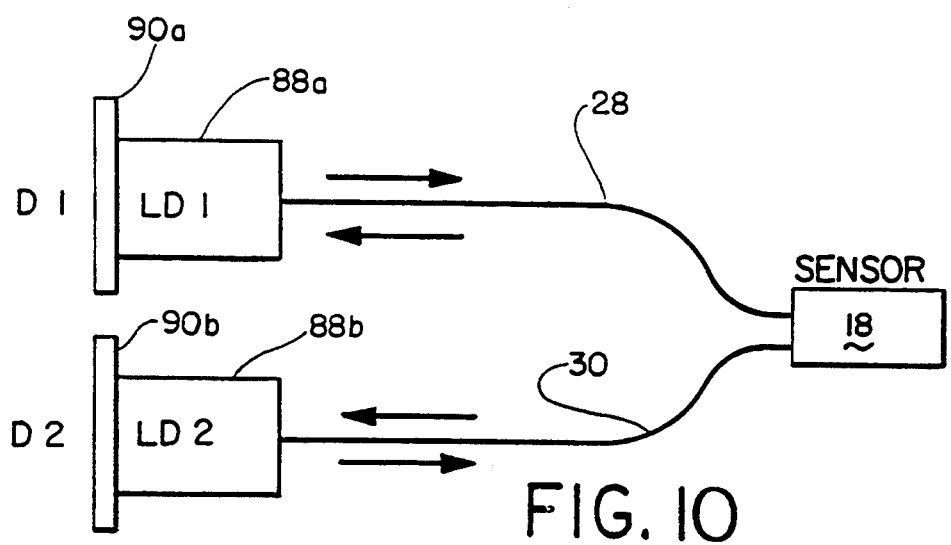

FIGS. 8–10 schematically illustrate alternative designs and methods for arranging the light sources 44 and detectors 46. In FIG. 8, two sources 44a,b and two detectors 46a,b are used for each optical fiber 28,30. Each source and detector pair are optically connected to their respective optical fiber 28,30 by a secondary fiber and a coupler 80,82. The coupler simply acts as an optical splitter in which the reflected light received during the detect cycle is directed both to the source and the detector. This approach operates satisfactory but is less preferred because of the added number of components, and reduced intensity of light incident on the detectors.

FIG. 9 represents how the invention can be realized by using only one source 44 and one detector 46. An optical switch 84 is placed in the optical path between the source/detector pair and the optical fibers 28,30. The optical switch, controlled by appropriate electronic circuits (not shown), alternately connect the light emitted from the source 44 to the optical fibers 28,30, thereby achieving the bi-directional interrogation of the sensor 18. Whenever the switch 84 optically connects the source to one of the fibers 28,30, at the same time it optically connects the other fiber to the detector 46. This approach has the advantage of not requiring normalization of the source/detector electro-optical characteristics; but the tradeoff is that commercially available optical switches for multimode optical fibers only operate up to about 20 Hz.

FIG. 10 illustrates how the invention can be realized by the use of a combined source/detector pair 88,90 housed in a common receptacle for each respective fiber 28,30. For example, this embodiment can be realized with a laser diode that has a back facet detector. The back facet detector can automatically sense the emitted light intensity when its respective source is activated. It can be also be realized using LEDs by allowing the LEDs to function as both optical source and detector as in FIG. 1.

Those skilled in the art will also appreciate that the present invention can be realized without the use of a folded optical path, wherein the mirror is omitted and the second optical fiber receives the light exiting from the magneto-optic material through a second lens. The folded path is preferred for compact size and more convenient isolation of the optical sensor assembly from the fluid. The folded optical path also causes each light interrogation to pass through the magneto-optic material twice providing a larger rotation of the polarization angle and hence a more easily detected change in the output light intensity.

E. Preferred Embodiment of A Proximity Sensor

Figure 11:
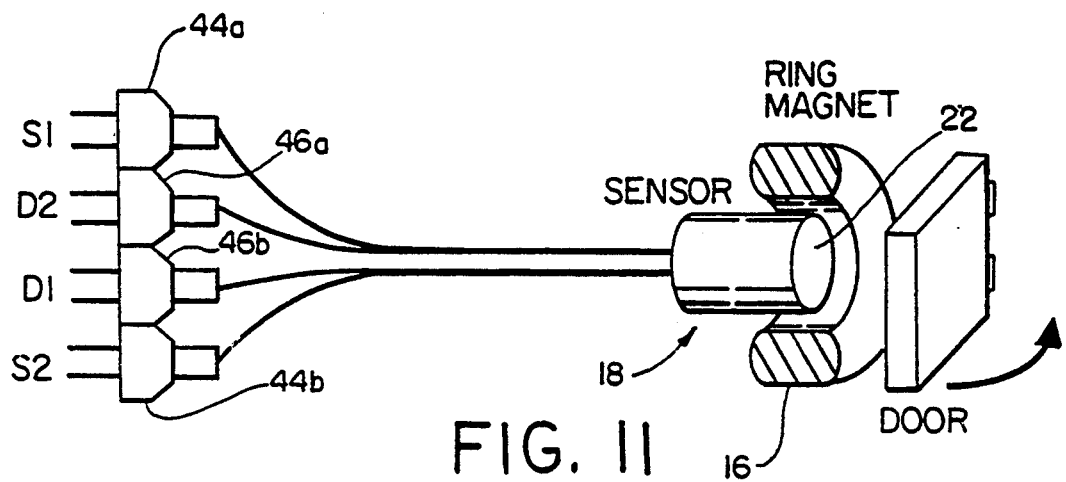
FIG. 11 is a simplified schematic of an optical sensor according to the present invention used to realize a proximity sensor.
Figure 12:
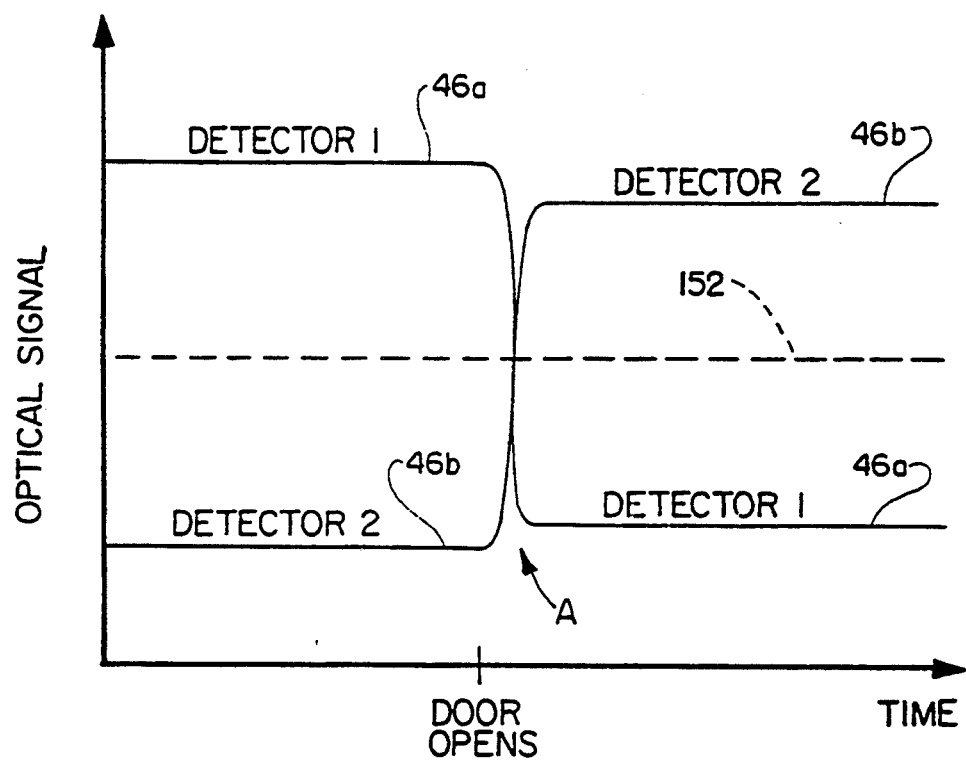
FIG. 12 is a graphical representation showing typical expected detector output signals for a proximity detector in accordance with the present invention.
Figure 13:
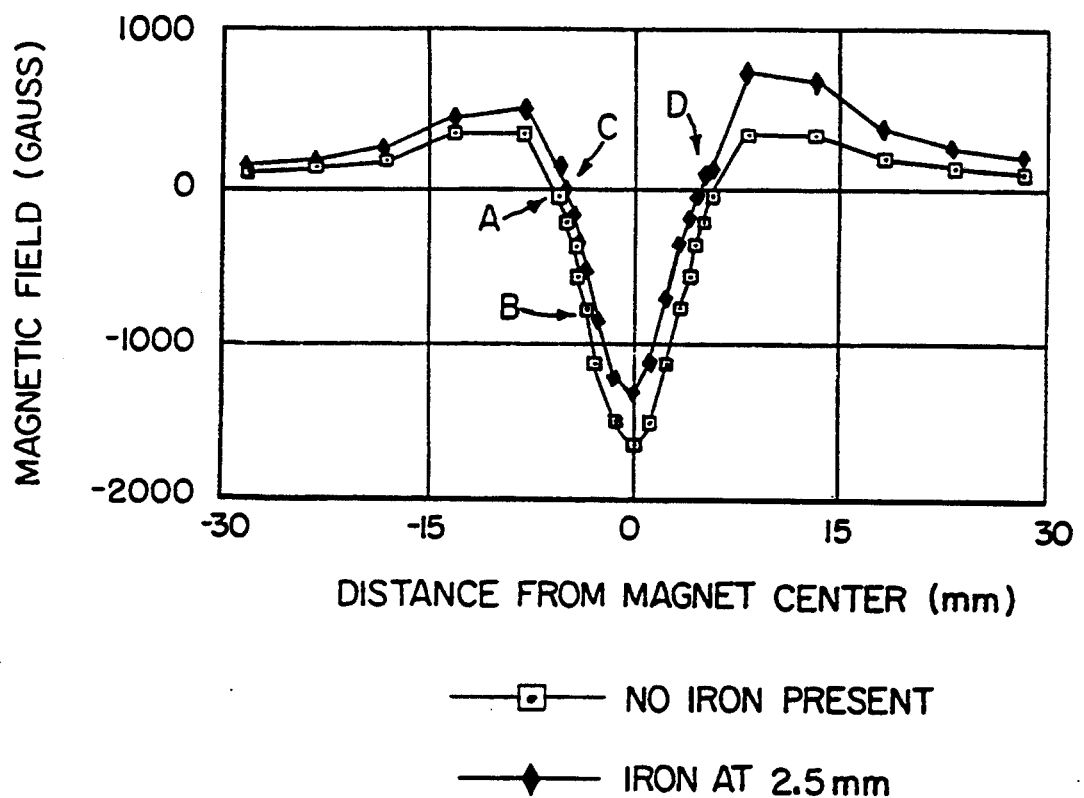
FIG. 13 is a graphical representation of axial magnetic field versus distance for a ring magnet for the conditions of no ferrous target and a ferrous target in close proximity to an optical sensor according to the present invention.

The optical sensor 18 configuration illustrated in FIGS. 1 and 2 and explained hereinabove can be modified to function as a proximity detector or switch as illustrated in FIGS. 11–13. The basic operation of a proximity detector is to provide an output signal or indication that a target object has moved to within or away from a predetermined threshold distance from the sensor head. Typically, proximity detectors act as binary devices, having one output state when the threshold condition is satisfied, and another output state when the threshold condition is not satisfied.

Using the optical sensor 18 as a proximity detector involves several different design criteria compared to the debris monitor application. To begin with, first recall that in the debris monitor the optical sensor 18 operates in a linear mode with respect to the magnetic field. That is, as ferrous debris accumulates on the magnet, there is preferably a generally linear change in the magnetic field portion that passes through the magneto-optic material 22. The sensor 18 is positioned near a node of the magnet so as to best operate within this linear region as the node shifts towards the center of the magnet. It is contemplated, of course, that in some applications the debris monitor is operated in such a manner that the node actually "passes through" the magneto-optic material 22 as more and more debris accumulates on the probe 10.

As illustrated in FIG. 13, the magnetic field portion passing through the magneto-optic material 22 changes polarity as the node is drawn through the material 22. This change in polarity (i.e. direction) of the magnetic field causes a change in the polarity of $\theta m$ relative to the fixed polarizers 34,36. Consequently, the detector 44a,b outputs invert as described hereinbefore because the optical path is non-reciprocal. In other words, with reference to FIG. 12, the detectors have changed from operating on one side of the point A to the other side. Because the detector outputs invert as the magnetic node passes through the magneto-optic material 22, the output 64 of the difference-over-sum circuit necessarily changes polarity.

In a debris monitor, the polarity changes caused by the node moving through the magneto-optic material 22 can be used for convenience such as a go/no-go test or other threshold limit function based on quantity of debris accumulation on the probe 10. But, typically the more important data is the gradual change in the magnetic field detected over time as the debris accumulates.

The polarity reversal, however, provides an excellent indication for use in a proximity detector. As a proximity detector, the apparatus of FIG. 11 detects the polarity reversal caused as a ferrous target reaches a threshold position near the optical sensor. By proper selection of the magneto-optic material, the magnet dimensions and positioning of the sensor material 22 with respect to the magnetic node, the device of FIG. 11 provides a highly accurate proximity switch.

For example, with reference to FIG. 11, assume that a proximity switch is needed for determining whether a door is open or closed. The sensor configuration is illustrated in a simplified manner in FIG. 11 to more clearly show the difference from the debris monitor configuration. Also, FIG. 11 shows the use of dual light source/detector pairs, though single devices as explained hereinbefore can also be conveniently used (in FIG. 11, the same numerals are used for elements corresponding to like elements in FIGS. 1–10). The probe 10 is positioned near the door so that when the door is in one state, for example open, the detector 44a,b outputs provide a difference-over-sum output signal 64 of one polarity. When the door is closed as shown in FIG. 11, a magnetic or ferrous target actuated with the door is positioned near the probe 10 so as to modify the magnetic field of the probe 10 and completely draw the magnetic node through the magneto-optic material. This affects a change in the polarity of the magnetic field, and hence the ratio output 64 switches polarity. A simple level detector 150, shown in phantom in FIG. 2, can be used to detect the polarity change and hence the position of the door.

FIG. 12 illustrates graphically the detector 46a,b outputs when the optical sensor 18 is used as a proximity detector. Essentially, the devices are operated in the saturation regions where the only data of real interest is the relative value of the inversely related detector 46a,b outputs. At point A an event occurs, such as opening or closing a door. This causes the detector 46a,b outputs to flip states thus causing a change in polarity of the differences-over-sum circuit output 64. The dashed line 152 in FIG. 12 represents the average or null value of the detector outputs when zero magnetic field is present in the magneto-optic material 22.

With a proximity detector, the transition region between the inverted saturated states is not of primary interest. Therefore, to minimize the effect of the transition region, a magneto-optic material such as LLC made by Litton Airtron is used that exhibits a higher hysteresis and causes a more pronounced change in rotation angle of the interrogation light at lower magnetic fields. The debris monitor, on the other hand, preferably uses a lower hysteresis material with smaller rotation characteristics per unit gauss because the debris monitor is more dependant on detecting smaller variations in the magnetic field as debris accumulates.

Also, in the proximity detector, it is preferred to use a magnet that is less sensitive to the accumulation of ferrous particles on the magnet. Therefore, a designer should select a magnet in which the outer diameter will not predominate over the inner diameter. This will prevent significant changes in the magnetic field simply due to particle accumulation on the magnet. This is in contrast, of course, to the debris monitor application in which it is preferred that the magnetic field undergo pronounced variations with even small accumulations of debris.

Furthermore, with respect to the position of the magneto-optic material 22 relative to the magnet 16, in a proximity detector the material is placed such that as the target moves from a first position to the threshold position, or vice-versa, the node is completely pulled through the material 22. With reference to FIG. 13, a ferrous target close to the magnet causes the response curve to move towards the target. Thus, the magneto-optic material 22 for a proximity detector should be positioned behind the magnetic node closest to the ferrous target such as at position D noted on FIG. 13. Thus when the target moves into position, the magnetic node will be pulled through the magneto-optic material 22. The distance of the ferrous target from the magnet will determine how much change in the magnetic field is induced. The further the target is from the magnet 16, the less pronounced will be the magnetic field change. In contrast, as stated previously herein with reference to the debris monitor, accumulation of debris on the magnet causes the response curve of FIG. 4 to narrow. Therefore, the material 22 is positioned behind the node. Also, the node as an event indicator is more a matter of design choice for the debris monitor application.

The PIN diode feedback arrangement used to regulate the source 44 intensity in the debris monitor application is not needed in the proximity detector because the modulation in light intensity induced by the pronounced magnetic field change from movement of the target is substantially greater than intensity variations over time and temperature.

Those skilled in the art will readily appreciate that the proximity sensor application employs all the advantages and benefits of our invention described hereinbefore. The optical sensor 18 still functions as a bi-directionally addressed non-reciprocal sensor that is inherently self-referenced to remove errors caused by light intensity changes due to causes other than movement of the target. Also, the difference over sum signal processing contains the same built in test capability that alerts an operator if one or more of the channels is inoperative. An indication of plus (+) or minus (−) one indicates a channel failure. Again, since the output of the circuit of FIG. 2 is a continual real-time indication of the target position, any number of proximity detectors can be used in a multiplexed data processing system. The alternative embodiments of FIGS. 8–10 are also similarly useful with a proximity detector.

F. Summary

The proximity detector described hereinabove in accordance with the present invention provides a compact, easily manufactured detector that is self-referenced using the same optical signals used to detect the target proximity, and further includes an inherent built-in test feature. The optical sensor provides a bi-directionally addressed sensing scheme that is self-referenced and utilizes a single interrogation light wavelength and a single non-reciprocal optical path.

The debris monitor system and optical sensor and methods of using the same described hereinabove realize a completely self-contained debris detector and accumulator that is self-referenced and has a built-in-test capability. A single wavelength of light is input to the optical sensor through each of the optical fibers coupled to the sensor. This bi-directional interrogation of the magneto-optic material makes the system immune to light intensity changes such as variations in line and connector losses. The output comparison of the electro-optical transducer is therefore only a function of the magnetic field induced rotation in the received light's angle of polarization. Because the optical sensor assembly is non-reciprocal, a ratio calculation such as difference over sum signal processing of signals obtained through bi-directional interrogation or address of the sensor makes the device self-referencing. Polarity change of the difference-over-sum ratio can be used as a threshold detector for a go/no-go design feature or for a proximity detector. Built-in-test function can be incorporated because sensor failure is indicated when the ratio signal becomes either plus (+) or minus (−) one.

The debris monitor system contemplated by our invention as disclosed herein monitors total accumulating of debris on a magnet and provides rate of accumulation data based on the differentiated ratio output signal. Our debris monitor system samples the entire size spectrum of magnetic particles in a fluid so that failure modes indicated by particle generation can be detected regardless of the particle size manifested during the failure. Because the debris monitor utilizes modulation of magnetic field due to accumulation of particles on the magnetic probe, the system has inherent memory. The output can be monitored continuously, periodically or by maintenance crews carrying electronic units that interrogate the optical sensor under a routine service schedule. Several systems can be multiplexed to a single electro-optical transducer and signal processor.

While the invention has been shown and described with respect to specific embodiments thereof, this is for the purpose of illustration rather than limitation, and other variations and modifications of the specific embodiments herein shown and described will be apparent to those skilled in the art within the intended spirit and scope of the invention as set forth in the appended claims.

I claim:

1. A proximity detector for detecting position of a ferromagnetic target comprising a permanent magnet having a magnetic field portion that changes in response to movement of the target, and a magneto-optic sensor that detects said magnetic field portion change, said magneto-optic sensor including a magneto-optic material positioned within said magnetic field portion, means that transmits polarized light bidirectionally along an optical path through said magneto-optic material, said magneto-optic material rotating said light angle of polarization in relation to said magnetic field portion; and means to detect said polarization angle rotation.

2. The proximity detector according to claim 1 wherein said bidirectional optical path is non-reciprocal such that the output intensity of light that travels in one direction along said optical path is inversely related to the output intensity of light that travels in the opposite direction along said optical path.

3. The proximity detector according to claim 2 wherein said magneto-optic material is positioned near a node of said magnet such that movement of the target from a first position to a second position causes said magnetic node to pass through said magneto-optic material.

4. The proximity detector according to claim 2 wherein said means to detect said polarization angle rotation includes a pair of polarizers in said optical path and a pair of light detectors that produce outputs related to the intensity of light thereon, said detectors being exposed to light that has passed bidirectionally through said magneto-optic material and said polarizers.

5. The proximity detector according to claim 4 wherein said optical path is a folded optical path, said light detectors producing outputs related to the intensity of light bidirectionally transmitted that has passed through said magneto-optic material twice and through said polarizers.

6. The proximity detector according to claim 5 further comprising means to compute a ratio of two of said detector outputs produced in response to a bidirectional address of said magneto-optical material.

7. The proximity detector according to claim 6 wherein said ratio is defined as the difference divided by the sum of said detector outputs.

* * * * *